United States Patent [19] [11] 3,985,805
Norton [45] Oct. 12, 1976

[54] PREPARATION OF ALKYLCARBOXAMIDES

[75] Inventor: Richard V. Norton, Wilmington, Del.

[73] Assignee: Sun Ventures, Inc., St. Davids, Pa.

[22] Filed: Oct. 1, 1975

[21] Appl. No.: 618,657

Related U.S. Application Data

[63] Continuation-in-part of Ser. No. 409,484, Oct. 25, 1973, abandoned.

[52] U.S. Cl. .......................... 260/558 R; 260/561 R
[51] Int. Cl.$^2$ ............... C07C 102/08; C07C 103/76
[58] Field of Search ..................... 260/558 R, 561 R

[56] References Cited
UNITED STATES PATENTS
3,825,596   7/1974   Naito et al. ..................... 260/558 R

OTHER PUBLICATIONS

*Synthetic Organic Chemistry*, Wagner et al., pp. 568, 570, Wiley and Sons, Inc. (1953).

*Unit Processes in Organic Synthesis*, Groggins, 3rd Ed., pp. 680–681, McGraw Hill (1947).

*The Chemistry of the Amino Group*, Patai (Ed.), Interscience (1968), pp. 287–288.

Primary Examiner—Robert V. Hines
Assistant Examiner—Thomas A. Waltz
Attorney, Agent, or Firm—J. Edward Hess; Donald R. Johnson; Paul Lipsitz

[57] ABSTRACT

A process for the preparation of N-substituted alkylcarboxamides from a nitrile which comprises subjecting said nitrile to an aqueous non-catalytic hydrolysis to obtain an essentially equilibrium mixture consisting essentially of carboxamide and ammonium carboxylate salt, cooling said equilibrium mixture and isolating a crystalline mixture of carboxamide and ammonium carboxylate, reacting an alkylamine with the isolated mixture, filtering the reaction mass to separate insoluble carboxamide, and contacting the filtrate with a dehydration catalyst to obtain said N-substituted alkylcarboxamide in high yield.

7 Claims, No Drawings

PREPARATION OF ALKYLCARBOXAMIDES

CROSS REFERENCE TO RELATED APPLICATIONS

This is a continuation-in-part of application Ser. No. 409,484, filed Oct. 25, 1973 and now abandoned.

It is known in the art that an aromatic nitrile such as toluonitrile may be converted to the corresponding amide by aqueous reaction with an amine preferably in the presence of a catalyst such as mercuric chloride, hydrogen peroxide, and the like. Such processes as reported in Japan No. 73,00,543 and U.S. Pat. No. 3,758,576 generally give low yield of the product. Furthermore, the use of metal salt catalysts in the hydrolysis, which are required by the prior art processes for improved yields, cause corrosion of equipment, add to costs and result in a generally unsatisfactory process.

The present invention provides a novel method for making N-substituted alkylcarboxamides in high yields from the corresponding nitrile and a mono- or dialkylamine, and the process of this invention involves hydrolysis of the organic nitrile in the absence of any added catalyst. In accord with the invention N-alkylcarboxamides and N,N-dialkylcarboxamides are prepared by subjecting a nitrile to an aqueous, non-catalytic hydrolysis to obtain an equilibrium mixture consisting essentially of carboxamide and ammonium carboxylate salt, cooling the equilibrium mixture and isolating therefrom a crystalline mixture of carboxamide and ammonium carboxylate, reacting an alkylamine with said isolated mixture at a temperature of from about 20° to about 200° C. whereby the ammonium salt reacts with the amine, filtering the reaction mass to separate insoluble carboxamide, and contacting the filtrate with a dehydration catalyst to obtain said N,N-dialkylcarboxamide in high yield.

The following chemical equations illustrate the complete reaction process:

$$RCN \xrightarrow{H_2O} RCONH_2 \xrightleftharpoons{H_2O} RCOONH_4$$

$$RCOONH_4 + R'NH_2 \xrightarrow{20-200°\ C} RCOONH_3R' + NH_3$$

$$RCOONH_3R' \xrightarrow[300°-400°\ C]{catalyst} RCONHR' + H_2O$$

As is clear from the above equations applicant's process involves:

Firstly: a non-catalytic equilibrium hydrolysis of a nitrile; e.g.,

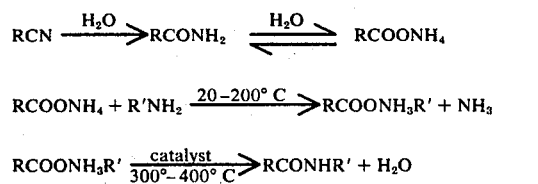

It should be noted that the carboxamide is unwanted and can be considered as a by-product.

Secondly: a crystalline mixture of the by-product carboxamide and the ammonium salt is separated from the equilibrium hydrolysis mass and an amine is added which reacts with the ammonium salt, but not the carboxamide, to give an amine salt carboxylate; e.g.:

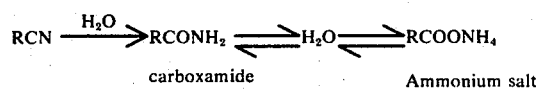

The by-product carboxamide does not take part in the reaction and is still present as insoluble crystals. After the insoluble, unreacted carboxamide is separated from the soluble amine carboxylate salt, then the filtrate containing the soluble amine salt carboxylate is dehydrated in a third reactive step; e.g.:

$$RCOONH_3R' \xrightarrow[300°-400°\ C]{cat.} RCONHR' + H_2O$$
N-Alkyl carboxamide product.

In the above manner, the N-alkyl carboxamide is obtained in surprisingly high yield being on the order of 70-95$^+$% yield based on hydrolyzate.

The initial hydrolysis of the nitrile will be made to occur in a closed reactor system at elevated temperature and pressure. Usually the conditions of reaction will be between about 200° and 350° C. under autogenous pressure and will be completed in usually from about 0.5 to 20 hours. The equilibrium that will be obtained under such conditions may be illustrated by the following equations:

$$RCN \xrightarrow[(a)]{H_2O} R-\overset{O}{\underset{\|}{C}}-NH_2 \xrightleftharpoons[(b)]{H_2O} R-\overset{O}{\underset{\|}{C}}-ONH_4$$

It will be understood that the equilibrium of reaction (a) is shifted almost completely to the right by reaction (b) and thus little or no nitrile is present in the final equilibrium hydrolysis mixture. When equilibrium is established the mixture will contain about 25% (molar) of carboxamide and 75% of the ammonium carboxylate salt. Infrared analysis to show the essential absence of nitrile function at 4.5u, or titration of —COONH$_4$ groups is a useful guide to determining when equilibrium is established. After equilibrium has been established the reaction mass is cooled to a temperature of from about 50° to about 100° C. whereby a mixture of carboxamide and ammonium carboxylate precipitates. It may be necessary prior to the cooling step, if very soluble materials are being used, to concentrate the hydrolysis mixture in order to assure complete separation of the carboxamide and ammonium carboxylate mixture. At any rate, the crystalline mass, which, as indicated, consists essentially of the ammonium salt and carboxamide, is separated from the remaining nitrile either by filtration, centrifugation, or other means.

The crystalline product is then treated with the desired mono- or dialkylamine by slurrying it in the alkylamine, generally using from 1.5 to 5 moles of dialkylamine per mole of the functional —CONH$_2$ and —COONH$_4$ groups. The temperature of this treatment is not critical, but may be determined by the available equipment. However the higher temperatures, preferably at the reflux temperature of the amine, promote rapid ammonia release as compared to the lower temperature. For amines boiling less than 125° C, pressure equipment is preferred. Generally the slurrying will be made to occur at temperatures between about room temperature (e.g. 20° C) up to about 200° C.

After the slurry has been digested for about 1 hour to about 5 hours and evolution of ammonia vapors has essentially stopped, it is subjected to a vacuum or pressure filtration to remove the insoluble carboxamide hydrolysis intermediates, leaving the ammonium carboxylate dissolved in the alkylamine. The ammonium salt-dialkylamine solution may be decolorized at this point by a charcoal treatment and is subsequently contacted with dehydration catalyst to convert the reactants to the desired alkylcarboxamide. A suitable technique to accomplish this is to employ as catalyst a phosphoric acid treated silica gel which is placed in a reactor tube and the dialkylamine solution allowed to drip through the catalyst bed in the reactor at elevated temperature (usually about 300° to about 400° C). A stream of nitrogen swept through the bed and into a collection receiver may be used to assist in moving the reactants and products through the bed. After a short period of operation, generally not more than 1 to 3 hours, the dialkylamine solution is entirely reacted and the product is water washed and vacuumed distilled. Catalysts which may be used for this step will be the well known dehydration catalysts, such as the various inert metal oxides typified by alumina, silica, magnesia, boria, titania, and the like. As is known in the art these materials are often treated with an acid such as phosphoric acid to enhance their catalytic activities and such practice may be employed here.

The nitriles useful in the process may be selected from a wide variety of alkyl and aromatic nitriles and in general the nitriles will be selected from those having the structure $R_1$—CN where $R_1$ is an alkyl group of 1 to 18 carbon atoms (preferably 1 to 6 carbon atoms) and the structure $R_2$—$(CN)_n$ where $R_2$ is an aromatic hydrocarbon group containing 6 to 12 carbon atoms and $n$ is a small integer (e.g. 1, 2, or 3). Specific nitriles useful in the process are and exemplified by acetonitrile, propionitrile, butyronitrile, heptanonitrile, undecanonitrile, benzonitrile, toluonitrile, terephthalonitrile, isophthalonitrile, 1-cyanonaphthalene, 2,6-dicyanonaphthalene, and the like. Preferably the reaction will be carried out with nitriles where $R_1$ is a lower alkyl group and $R_2$ is an aromatic group of the benzene series. Preferred nitriles of the benzene series include benzonitrile, toluonitrile, and terephthalonitrile. The amines used in the reaction will be primary and secondary amines of the structure

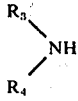

where $R_3$ is H or the same as $R_4$ which is an alkyl group of 1 to 18 carbon atoms. Preferably lower alkyl amines (e.g. those having alkyl groups of 1 to 6 carbon atoms) will be used. Preferred amines are methylamine, diethylamine, ethylamine, dipropylamine, isopropylamine, di-isobutylamine, and the like.

In order to further illustrate the invention the following examples are given.

EXAMPLE I m-Toluonitrile (2.5 moles) was hydrolyzed in a stainless steel reactor containing 1 liter of water at 300° C, 1200 psig for 18 hours. After cooling to room temperature the insoluble salts and amide were separated by filtration and dissolved in 2 moles of anhydrous diethylamine. The insoluble amide and salts accounted for 43 mole % of m-toluonitrile charge. The filtrate was recycled for hydrolysis with more m-toluonitrile.

After stirring the diethylamine slurry for 1 hour at 100° C in pressure equipment and then cooling to 20° C the mixture was filtered in vacuo. The insoluble material represented 10 mole % of the m-toluonitrile charge.

The diethylamine solution filtrate was passed through an amidation reactor comprising a tube charged with a phosphoric acid treated silica gel catalyst at 305° C for a contact time of 0.1 sec. using $N_2$ as a sweep gas.

The product which condensed was purified by fractional distillation to give, N,N-diethyltoluamide in 95+% yield based on moles of hydrolyzate charged to the amidation reactor.

EXAMPLE II

In the manner of Example I, acetonitrile was hydrolyzed at 250° C for 20 hours and the acetamide and ammonium salts separated by filtration. After slurrying the insolubles with diethylamine, heating at 100° C. and filtering, the filtrate solution was passed over an alumina catalyst. The product effluent was purified by fractional distillation to give diethylacetamide in high yield.

EXAMPLE III

Terephthalonitrile (0.1 mole) was hydrolyzed in water (500 cc) at 250° C for 1 hour and cooled to 80° C by flash vaporization. The damp crystals of hydrolyzate product were slurred in N-butylamine (100 ml) and refluxed at 78° C for 3 hours to effectuate ammonia removal. The hot solution was then passed through a phosphoric acid treated silica gel catalyst bed at 400° C and the products collected in an ice bath.

Concentration of the product followed by crystallization gave di-n-butyl terephthalamide in 70% yield.

The invention claimed is:

1. A process for the preparation of an N-alkylcarboxamide from a nitrile which consists of subjecting a nitrile of structure $R_1$—CN or $R_2$—$(CN)_n$ where $R_1$ is alkyl of 1 to 18 carbon and $R_2$ is an aromatic hydrocarbon containing from 6 to 12 carbon atoms and $n$ is a small integer of 1, 2, or 3 to an aqueous non-catalytic hydrolysis at a temperature of from about 200° to about 350° C. to obtain from said nitrile, an equilibrium mixture consisting essentially of about 25 molar percent carboxamide and about 75 molar percent of ammonium carboxylate salt, cooling said equilibrium mixture and separating a crystalline mixture of said carboxamide and ammonium carboxylate, treating the crystalline product with an amine of structure $R_3R_4NH$ where $R_3$ is hydrogen or $R_4$, $R_4$ being alkyl of 1 to 18 carbon atoms, to obtain a mixture of the soluble amine salt of said carboxylate and unreacted carboxamide, separating insoluble unreacted carboxamide from the reaction mass, contacting the filtrate containing the amine salt of said carboxylate with a dehydration catalyst to effect dehydration to an alkylcarboxamide, and separating said N-alkylcarboxamide product in high yield.

2. A process for the preparation of an N-alkylcarboxamide or an N,N-dialkylcarboxamide from a nitrile which consists of subjecting a nitrile structure $R_1$—CN or $R_2$—$(CN)_2$ where $R_1$ is alkyl of 1 to 18 carbon atoms, and $R_2$ is aromatic hydrocarbon containing from 6 to 12 carbon atoms, to an aqueous non-catalytic hydrolysis at a temperature of from about 200° to about 350° C., to obtain from said nitrile an equilibrium mixture consisting essentially of about 25 molar percent carboxamide and about 75 molar percent of ammonium carboxylate salt, cooling said equilibrium mixture and isolating a crystalline mixture of carboxamide and ammonium carboxylate, treating the crystalline mixture with a primary or secondary lower alkylamine containing from 1 to 6 carbon atoms in the alkyl group to obtain a mixture of the soluble amine salt of said carboxylate and unreacted carboxamide, filtering the reaction mass to separate insoluble unreacted carboxamide, contacting the filtrate containing the amine salt of said carboxylate with a dehydration catalyst to effect dehydration to an alkylcarboxamide and separating N-alkylcarboxamide product in high yield.

3. The process of claim 2 where the nitrile is an aromatic nitrile of the benzene series.

4. The process of claim 3 where the nitrile is terephthalonitrile.

5. The process of claim 3 where the nitrile is toluonitrile.

6. The process of claim 2 where the nitrile is an aliphatic nitrile containing 1 to 6 carbon atoms.

7. The process of claim 6 where the nitrile is acetonitrile.

* * * * *